US006379042B1

(12) United States Patent
Polkus et al.

(10) Patent No.: US 6,379,042 B1
(45) Date of Patent: Apr. 30, 2002

(54) VARIABLE SELF-COMPENSATING DETENT CONTROL SYSTEM FOR IMPROVED POSITIONING ACCURACY AND REPEATABILITY

(75) Inventors: Vincent S. Polkus, Delafield; Mark Anthony Hammel; John Jun Zhang, both of Waukesha, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/575,035

(22) Filed: May 19, 2000

(51) Int. Cl.[7] ................................................ G01T 1/00
(52) U.S. Cl. ........................ 378/205; 378/196; 318/466; 318/626
(58) Field of Search .................................. 378/193, 194, 378/195, 196, 197, 114, 205; 318/626, 568.17, 594, 445, 466, 467, 468

(56) References Cited

U.S. PATENT DOCUMENTS 4,188,540 A * 2/1980 Reiniger ..................... 378/197

6,025,685 A * 2/2000 Paradayan .............. 318/468 X

* cited by examiner

*Primary Examiner*—David P. Porta
(74) *Attorney, Agent, or Firm*—McAndrews, Held & Malloy, Ltd.; Peter J. Vogel; Michael A. Dellapenna

(57) ABSTRACT

A variable self-compensating detent control system for improved positioning accuracy and repeatability is provided. The detent control system provides a system for reducing positioning errors in the positioning of an X-Ray tube in an X-Ray imaging system, such as accurate and repeatable positioning of the X-Ray tube at detents. The control system preferably includes a sensor unit generating positional or velocity signals indicative of the position or velocity of the X-Ray tube and a microprocessor receiving the positional signals and determining an overshoot correction. The overshoot correction is used by the X-Ray system to control a locking system controlling the position of the X-Ray tube. The sensor unit may employ a potentiometer, a digital encoder, or preferably both in combination to determine the positional or velocity signals.

34 Claims, 9 Drawing Sheets

VARIABLE SELF-COMPENSATING DETENT CONTROL SYSTEM FOR IMPROVED POSITIONING ACCURACY AND REPEATABILITY

BACKGROUND OF THE INVENTION

The preferred embodiments of the present invention generally relates to improvements in a medical X-Ray imaging system, and more particularly relates to an improved positioning control for positioning an imaging X-Ray tube.

FIG. 1 illustrates an exemplary medical X-Ray imaging system 100. The imaging system 100 includes a X-Ray tube 110, a collimator 120, a table detector 130, an X-Ray table 140, a patient 150, and a clinical operator 160. In operation, a patient 150 to be imaged is placed upon the X-Ray table 140 as shown. A clinical operator 160, such as a radiologist or technologist, then positions the X-Ray tube 110 and collimator 120 at one of several pre-determined positions relative to the patient. Once the clinical operator has positioned the collimator 120 at the desired position, the X-ray tube 110 is energized and emits X-Rays. The X-Rays pass through the collimator 120 which directs the X-Rays through the patient to the table detector 130. The energy of the X-Rays passing through the patient is attenuated by the anatomical features of the patient 150. The table detector 130 detects the energy of the X-Rays and develops an image of the anatomical features of the patient 150.

The X-Ray tube 110 and collimator 120 are typically fixed together to form an X-Ray assembly and are typically able to move in three dimensions relative to the X-Ray table 140. That is, the collimator 120 may be moved upward or downward along the patient's 150 body, right to left across the patient's 150 body, and closer to or farther from the patient's 150 body in any of several fixed positions called detents. Each of the several fixed positions or detents may correspond to different X-Ray exposure and imaging parameters that have been predetermined in order to produce the clearest possible images of the patient 150. For example, placing the collimator 120 farther from the patient may result in a different parameter for dynamic range of energy of the X-Rays received by the detector 130.

Typically, imaging parameters are calibrated only for the several predetermined fixed positions, and not continually throughout the path of movement of the collimator 120. That is, the imaging parameters are typically configured for only a single, specific position, and may change rapidly as the collimator is moved. Thus, precise positioning of the collimator 120 helps provide clearer, more clinically relevant images of the patient 150.

Referring to FIG. 1, typically, an medical X-Ray imaging system may employ and configure detents to identify the several fixed imaging positions for radiographic examinations. As the collimator 120 is moved to one of several fixed imaging positions, a detent is engaged which holds the collimator 120 in the desired position while imaging takes place. Detents may be mechanical or electrical, however, detents employing electromagnetic locks and a position reference triggering device may preferably be employed because of, for example, better wear properties.

Positioning errors as small as a millimeter may significantly reduce the quality of the resulting image. For example, anatomical cutoff may occur due to misalignment or misregistration of the beam with respect to the detector. Improving positioning control of the X-Ray tube also aids in the repeatability of X-Ray images which may be of great importance in comparing X-Ray images taken at time intervals during a patient's treatment. Thus, a need exists for an improved X-Ray tube and collimator positioning system for a medical imaging system.

BRIEF SUMMARY OF THE INVENTION

The preferred embodiments of the present invention provide a system for reducing positioning errors of an X-Ray tube in an X-Ray imaging device. The system facilitates the accurate and repeatable positioning of the X-Ray tube at detents. A preferred embodiment of the present invention preferably includes a sensor unit generating positional or velocity signals indicative of the position or velocity of the X-Ray tube and a microprocessor receiving the positional signals and determining an overshoot correction. The overshoot correction is then used by the X-Ray system to control a locking system controlling the position of the X-Ray tube. The sensor unit may employ a potentiometer, a digital encoder, or preferably both in combination to determine the positional or velocity signals.

DETAILED DESCRIPTION OF THE INVENTION

Figure 1:
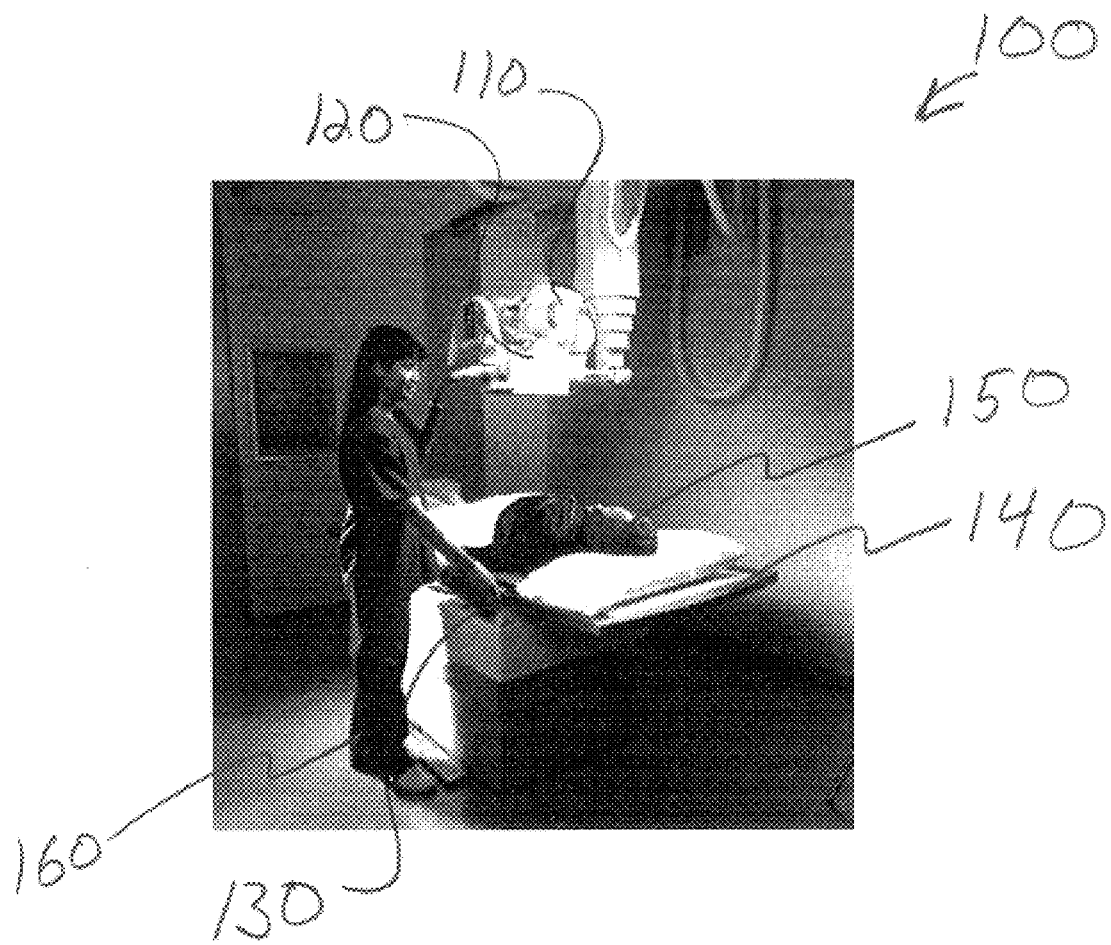
FIG. 1 illustrates a conventional exemplary medical X-Ray imaging system.
Figure 2:
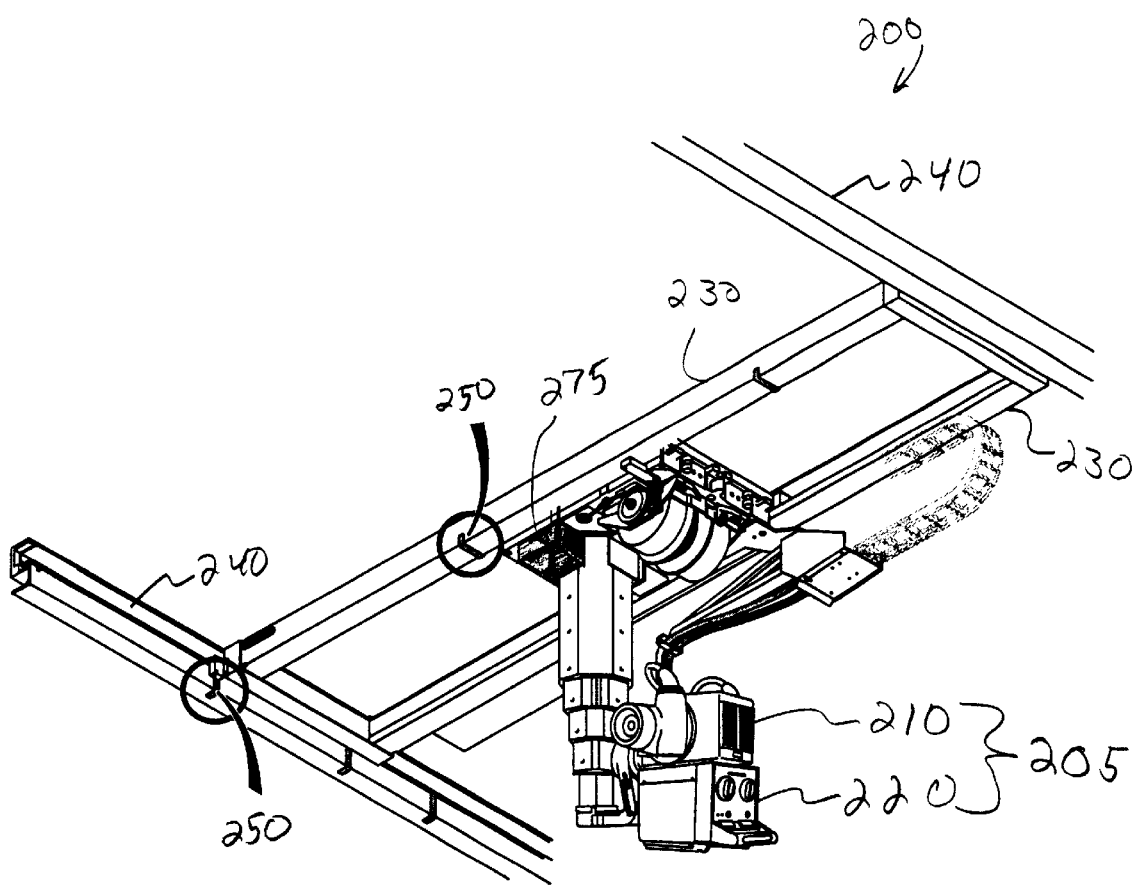
FIG. 2 illustrates an exemplary detent positioning system for a medical X-Ray imaging system according to a preferred embodiment of the present invention.

FIG. 2 illustrates an exemplary detent positioning system 200 for a medical X-Ray imaging system according to a preferred embodiment of the present invention. The detent positioning system 200 includes an X-Ray tube 210, a X-Ray assembly 205, a pair of vertical rails 230, a pair of horizontal rails 240, and a sensor unit 275. The X-Ray tube 210 and collimator 220 are collectively known as an X-Ray assembly 205. Both the horizontal rails 240 and the vertical rails 230 include a number of detents 250. In operation, the X-Ray assembly 205 is moved in two dimensions along the vertical rails 230 and horizontal rails 240, first by sliding the X-Ray assembly 205 and vertical rails 230 within the horizontal rails 240 to a detent 250 position on the horizontal rails 240. Then the X-Ray assembly 205 is slid within the vertical rails 230 to a detent 250 position on the vertical rails 230. Preferably, at each detent 250, electromagnetic locks are employed to lock the collimator in the desired detent position. The sensor unit 275 will be discussed below in detail.

Figure 3:
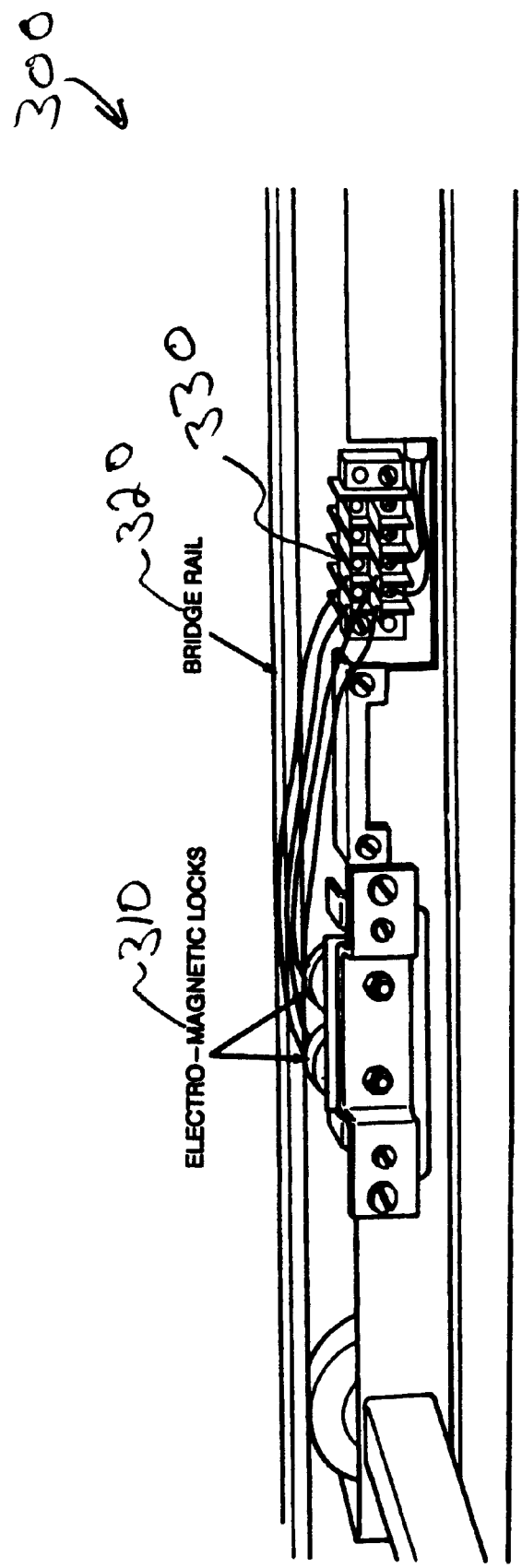
FIG. 3 illustrates a locking system of the medical X-Ray imaging system according to a preferred embodiment of the present invention.

FIG. 3 illustrates a locking system 300 of the medical X-Ray imaging system according to a preferred embodiment of the present invention. The locking system 300 includes electromagnetic locks 310, a bridge rail 320, and a power supply 330. In operation, the locking system 300 is mounted inside the vertical rails 230 and horizontal rails 240 of the detent positioning system 200 of FIG. 2. Once a given detent 250 position is reached, the electromagnetic locks 310 are activated and the position is locked in place. The electromagnetic locks 310 are activated by a voltage supplied by the power supply 330.

Figure 4:
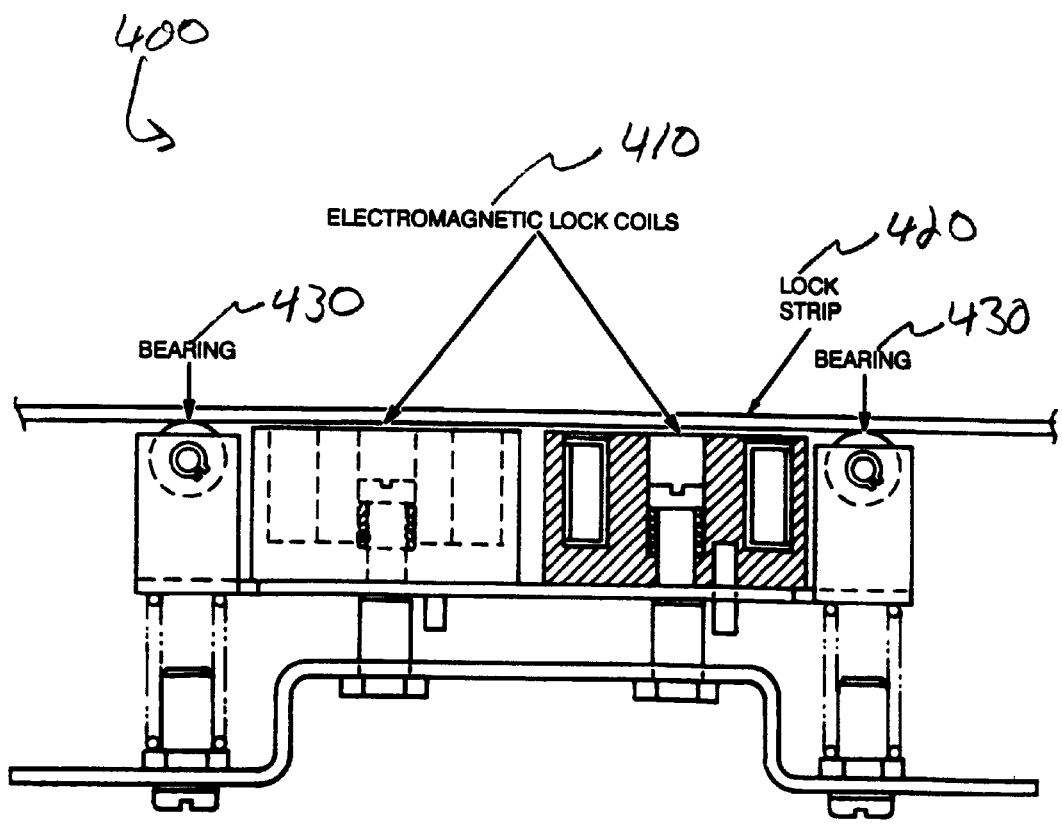
FIG. 4 illustrates a top view of the electromagnetic locks of FIG. 3 according to a preferred embodiment of the present invention.

FIG. 4 illustrates a top view 400 of the electromagnetic locks of FIG. 3 according to a preferred embodiment of the present invention. The view 400 includes electromagnetic lock coils 410, a lock strip 420, and bearings 430. In operation, as discussed above, the electromagnetic lock coils 410 may be slid inside a rail until they are activated by an externally supplied voltage. The externally supplied voltage generates a magnetic force between the electromagnetic lock coils 410 and the lock strip 420 sufficient to maintain and secure the collimator in a fixed position.

In operation, an electromagnetic lock requires a certain, finite time to develop sufficient magnetic force to begin decelerating the collimator 120. In addition, some time is required before the electromagnetic lock develops sufficient force to hold the collimator 120 in place. Referring to FIG. 2, because the X-Ray assembly 205 (and their support/positioning apparatus) have significant mass, and consequently significant momentum while being positioned by a clinical operator, the magnetic force generated by the electromagnetic locks may not be sufficient to overcome the momentum of the X-Ray assembly 205 within a desired time and, consequently, the X-Ray assembly 205 may not be stopped precisely at the desired detent. Thus, the activation and stopping time of the electromagnetic locks may introduce a positioning error in the positioning of the collimator. As mentioned above, this positioning error may adversely affect the quality and repeatability of the X-Ray images.

To put it another way, the speed at which the X-Ray assembly 205 is being positioned by an operator along with the electromagnetic lag or time delay of the electromagnetic lock may contribute to a final positioning error if the initial speed of the X-Ray assembly 205 is below a critical value ($V_c$). This positioning error is approximately proportional to the approach speed of the X-Ray assembly 205 to the detent position. However, if the speed of the X-Ray assembly 205 is sufficiently high, the electromagnetic lock may not react completely to engage and hold the device. If the electromagnetic lock does not engage completely, the X-Ray assembly 205 may simply pass through the intended detent location. Because the lock may not fully engage and hold the collimator at higher speeds, the operators must begin to slow down as they approach the detent position so that the X-Ray assembly 205 may be positioned and locked at the preset, pre-configured detent position. Additionally, unless the incoming speed is quite slow, the final offset positioning error may be significant, that is, from five to ten millimeters. Consequently, because the X-Ray assembly 205 must be moved slowly, additional time may be required. When additional time is required, customer productivity may be adversely affected because of the additional time per image.

In order to counter these effects, the preferred embodiment of the present invention calibrates a positional control system by measuring the detent positional overshoot at various approach speeds. The positional overshoot may be determined by using electronic feedback as further described below. Next, a transfer function between speed and overshoot is developed in order to determine the overshoot correction. Finally, the overshoot correction is applied to the collimator positioning during clinical use. Detent positional overshoot is preferably measured by using a microprocessor-based positioner control wherein both position and velocity feedback is available as described below with reference to FIGS. 8–10.

Figure 8:
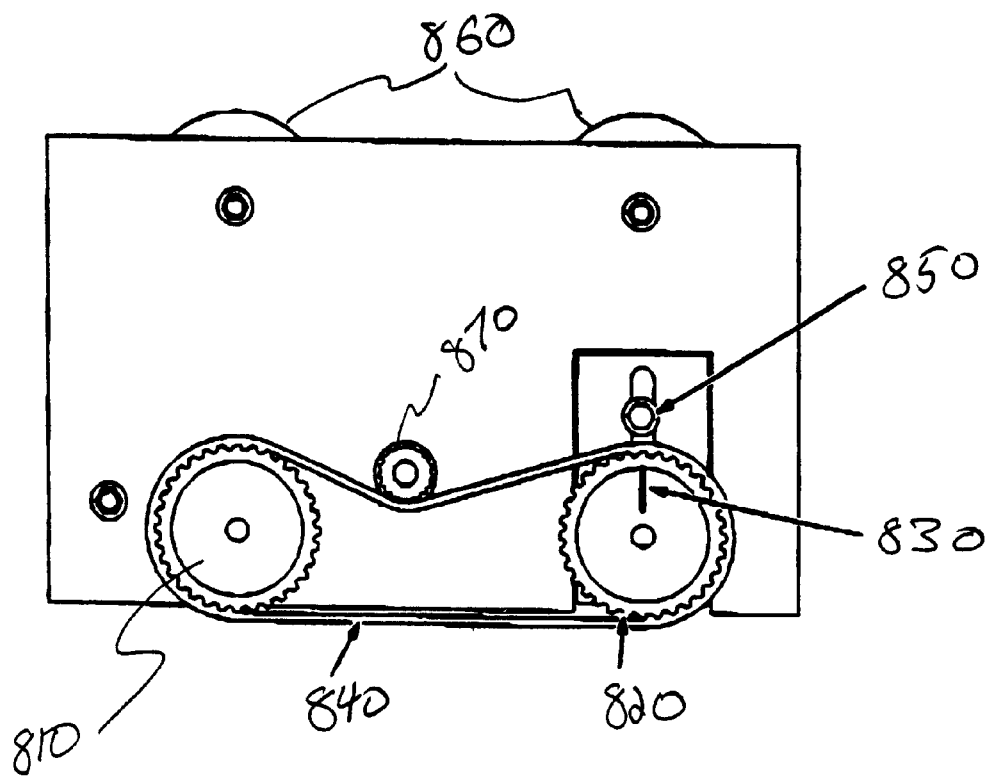
FIG. 8 illustrates a sensor unit according to a preferred embodiment of the present invention.

FIG. 8 illustrates a sensor unit 800 according to a preferred embodiment of the present invention. The sensor unit 800 includes an encoder sprocket 810, a potentiometer sprocket 820 having an alignment mark 830, a position sensor belt 840, a belt tensioner screw 850, a drive belt assembly 860, and a belt displacement sprocket 870. The position sensor belt 840 passes over the encoder sprocket 810 and the potentiometer sprocket 820. The tension on the position sensor belt 840 may be adjusted to a desired tension by use of the belt tensioner screw 850.

The X-Ray assembly, and thus the attached sensor unit 800 is typically manually positioned. Preferably, however, the sensor unit 800 is motor driven and positioned. For example, the sensor unit may be motor driven with a closed loop servo motor using the drive belt assembly 860. Positioning the sensor unit 800 using a motor, instead of manually, may help ensure consistent placement of the X-Ray assembly at the detent positions.

Figure 9:
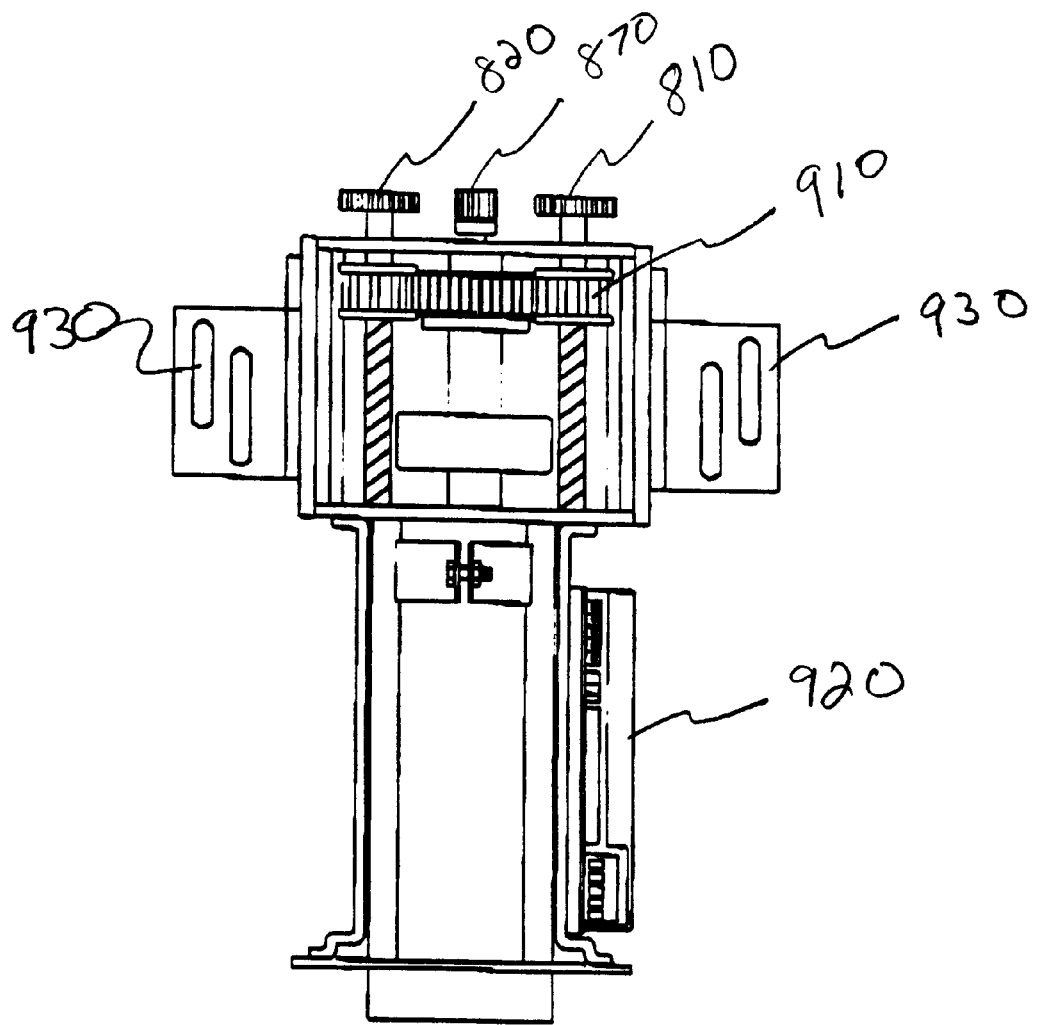
FIG. 9 illustrates a top view of the sensor unit 800 of FIG. 8 according to a preferred embodiment of the present invention.

FIG. 9 illustrates a top view 900 of the sensor unit 800 of FIG. 8 according to a preferred embodiment of the present invention. The encoder sprocket 810, potentiometer sprocket 820 and belt displacement sprocket 870 are shown. The sensor unit 800 also includes a drive belt assembly 910, a microprocessor interface 920, and securing points 930. The sensor unit 800 is preferably mounted on the X-Ray assembly as shown in FIG. 2 through the use of securing points 930.

In operation, the sensor unit 800 is associated with motion of the X-Ray assembly 205 along each of the rails. That is, one sensor unit 800 provides data concerning motion of the X-Ray assembly 205 along the pair of vertical rails 230 and one sensor unit provides data concerning motion along the pair of horizontal rails 240. A notched drive belt (not shown) is preferably mounted inside at least one of the pair of vertical rails 230 and in at least one of the pair of horizontal rails 240 of FIG. 2. The drive belt is preferably secured at each end of the rail and passes through the drive belt assembly 910 of the sensor unit 800 of FIG. 9. As the X-Ray assembly 205 is displaced, the fixed drive belt passing through the drive belt assembly 910 induces motion of the position sensor belt 840. The motion of the position sensor belt 840 induces revolution of the encoder sprocket 810 and the potentiometer sprocket 820.

The potentiometer sprocket 820 preferably includes an analog potentiometer. Preferably, a voltage is induced across the potentiometer so that the voltage changes with the rotation of the potentiometer sprocket 820, and thus with the position of the X-Ray assembly 205. The encoder sprocket 810 preferably includes a digital encoder. Preferably, the digital encoder provides data regarding the position and velocity of rotation of the encoder sprocket 810, and thus the position and velocity of the collimator. Preferably, the potentiometer sprocket 820 is used to establish an initial position for the X-Ray assembly 205 when the collimator is initially powered-up. The encoder sprocket 810 may be unable to provide this initial information because of data loss at the previous system shut-down. However, the initial position for the X-Ray assembly 205 is recoverable from the potentiometer sprocket 820 because the rotation of the potentiometer sprocket 820 alters its included potentiometer mechanically and thus avoids loss-of-power difficulties.

Once the initial position of the X-Ray assembly 205 has been established by the potentiometer sprocket 820, the encoder sprocket 810 may be employed to provide highly accurate position and velocity information. The digital encoder of the encoder sprocket 810 preferably provides a clean, digital signal indicating the position of the X-Ray assembly 205 which may be easily analyzed to determine velocity information. The potentiometer sprocket 820 may be utilized to provide positional information regarding the X-Ray assembly 205 throughout operation, but the digitally encoded signals from the encoder sprocket 810 may be easier and simpler to use.

The initial positional information determined by the potentiometer sprocket 820 and the positional and velocity information determined by the encoder sprocket 810 are passed to an external microprocessor (not shown) by means of the microprocessor interface 920. As further described below, the microprocessor may analyze the positional and velocity information of the X-Ray assembly 205 to control the activation of the electromagnetic locking system 300 of FIG. 3, above. The microprocessor is typically housed within an external system cabinet.

Before use, the sensor unit 800 is calibrated to the specific rail for which it is to provide positional and velocity information. The potentiometer insider the potentiometer sprocket 820 is preferably a multiple-turn potentiometer (most preferably a 10-turn potentiometer) with hard stops at each end of its travel To calibrate the system, the potentiometer may be first rotated to a hard stop and then rotated to the middle of the potentiometer's range (in the case of a 10-turn potentiometer, 5 turns). The sensor unit 800 including the potentiometer may then be positioned at the center of its path of movement along the rail and the drive belt assembly 910 and position sensor belt 840 engaged. Additionally, the sensor unit 800 may be calibrated by adjusting the tension of the position sensor belt 840 using the belt tensioner screw 850.

Figure 7:
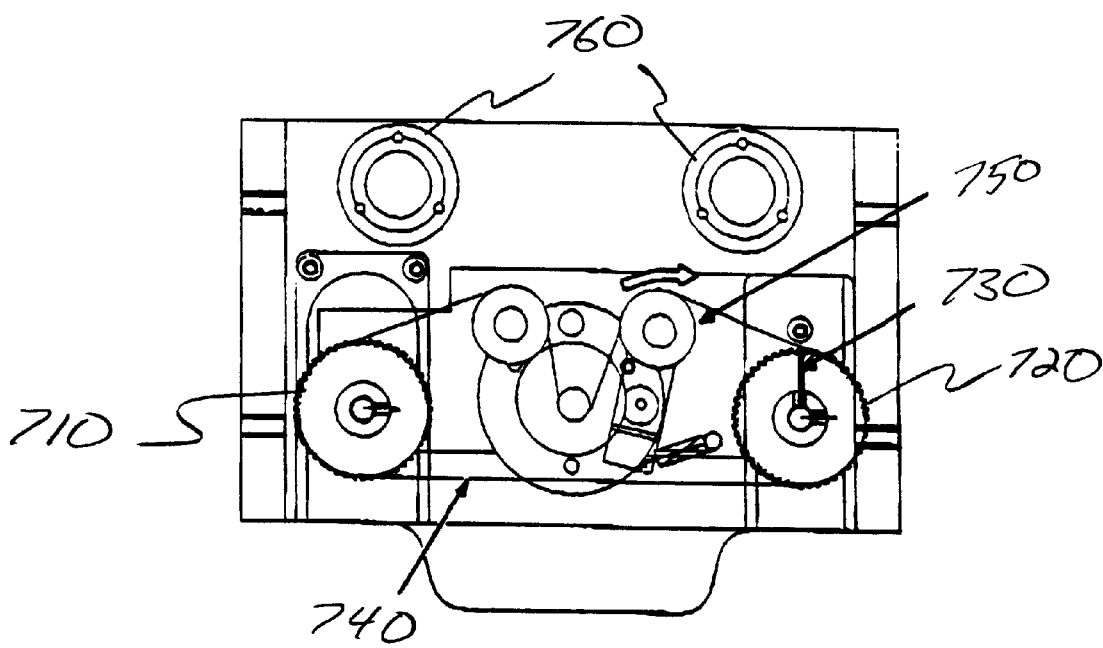
FIG. 7 illustrates a sensor unit with a self-tensioning belt assembly according to a preferred embodiment of the present invention.

FIG. 7 illustrates a sensor unit with a self-tensioning belt assembly 700 according to a preferred embodiment of the present invention. The self-tensioning belt assembly 700 includes an encoder sprocket 710, a potentiometer sprocket 720, an alignment mark 730, a position sensor belt 740, and a drive belt assembly 760, similar to the sensor unit 800 of FIG. 8. The self-tensioning sensor unit 700 also includes a tensioner arm 750, instead of the belt tensioner screw 850 of the sensor unit 800 of FIG. 8,which automatically applies a desired tension to the position sensor belt 740. Either the sensor unit 800 of FIG. 8 or the self-tensioning sensor unit 700 of FIG. 7 may be employed in the preferred embodiment of the present invention.

Once sensor unit has been selected and installed, the potentiometer sprocket of the sensor unit is calibrated and position sensor belts are engaged as described above. Then the assembly positioning system is calibrated. In order to calibrate the assembly positioning system, the collimator assembly is set into motion and information concerning the position and velocity of the collimator are sent to the microprocessor. A detent latch is then simulated. That is, power is applied to an electromagnetic lock on the X-Ray assembly and the assembly is brought to a halt. The position at which the assembly comes to rest may be different from the desired, predetermined, pre-configured, detent position. The difference in position between the detent position and the actual position of the assembly is then analyzed and an overshoot correction is determined.

Figure 5:
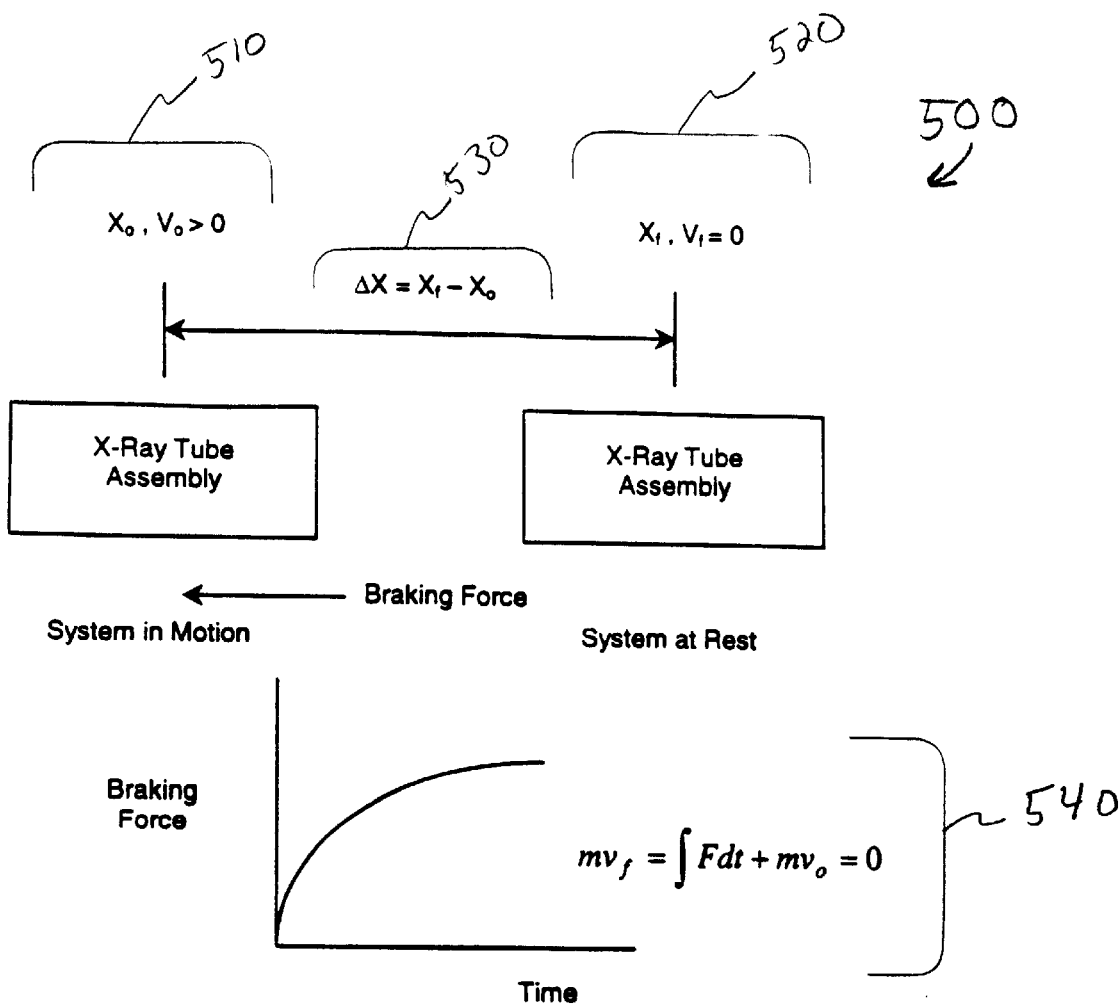
FIG. 5 illustrates a calibration sequence according to a preferred embodiment of the present invention.

FIG. 5 illustrates a calibration sequence 500 according to a preferred embodiment of the present invention. First, at location 510, the X-Ray tube assembly is in motion at some initial velocity, $V_o$, which is greater than zero and is located at an initial position, $X_o$, also greater then zero. Then, the electromagnetic lock is engaged. The electromagnetic lock applies a braking force in the opposite direction of the motion of the assembly. The tube assembly then comes to rest at location 520, that is, the final velocity $V_f$ is equal to zero and at the assembly is located at a final position $X_f$. Then the overshoot, $\Delta X$, the change in position between the initial position $X_o$ where the electromagnetic lock was activated and the final position $X_f$ where the assembly came to rest is determined at 530. Once the initial and final velocities and positions have been determined, the braking force may be determined at 540. The mass of the assembly is known and does not change during the calibration process. The calibration sequence is then repeated at several different initial velocities and an empirical relationship between the initial speed $V_o$ and the overshoot $\Delta X$ is determined to determine an overshoot correction.

The overshoot correction may, for example, be expressed as a linear relationship based on a least-squares regression fit of several speed-overshoot calibration tests. This linear relationship may be expressed as $$\Delta X = B_0 + B_1 V$$

Alternatively, the overshoot correction may, for example, be expressed as a more genera non-linear polynomial form such as:

$$\Delta X = A_0 + A_1 V_0 + A_2 V_0^2 + A_3 V_0^3 + A_4 V_4^4 + \ldots$$

where the order of the polynomial depends upon the number of discrete speeds incorporated in the calibration process.

Once the overshoot correction has been determined, the overshoot correction is used to determine the position at which the electromagnetic brake should be enabled by the system so that the assembly comes to rest at the desired detent position. That is, the calibration sequence determines the position at which the brake should be enabled by the system controller in order to minimize the position overshoot with respect to the detent position target, as a function of the initial velocity of the tube assembly.

A second embodiment of the present invention includes providing continuous positional error monitoring. That is, instead of only using the velocity and position references from an initial calibration process, continuous positional sensing is provided. If the detent positional error exceeds a certain maximum, the operator may be notified, the electromagnetic lock may disengage, and the operator may re-position the assembly.

A third embodiment of the present invention includes adaptively calibrating the offshoot correction by continuously updating the offshoot correction after each positioning of the tube assembly. That is, each time the assembly is positioned at a detent, the initial velocity and positional error are measured. The velocity and positional error measurements may then be used to generate a corrected offshoot correction for the assembly. This embodiment also allows the positioning system to compensate for system degradations that occur with use. For example, sustained use of the assembly may result in increased friction in the rails, which may cause the assembly to stop more quickly. By adaptively calibrating the offshoot correction, the effect of increased friction may be minimized and the assembly continuously positioned with minimal positional error.

By employing any of the embodiments of the present invention to generate an overshoot correction, the alignment between the X-Ray tube and detector assembly is made more accurate and repeatable than with existing implementations that employ only detents and that do not incorporate the velocity feedback and predictive algorithms of the preferred embodiments of the present invention.

The improvements in accuracy and repeatability of positioning provided by the present invention may also minimize radiographic re-takes associated with a variety of factors such as patient anatomical cutoff. Patient anatomical cutoff occurs when an X-Ray image does not contain the desired anatomical information and must be re-taken. Because one of the significant causes of patient anatomical cutoff is positioning error of the assembly, by minimizing positioning error of the assembly, patient anatomical cutoff may also be reduced. Additionally, the present invention may also improve customer productivity in a number of ways. For example, the operator may position the X-Ray assembly rapidly without fear of positional error. Thus, the speed of positioning the assembly is increased and the additional time associated with radiographic re-takes is minimized.

Figure 6:
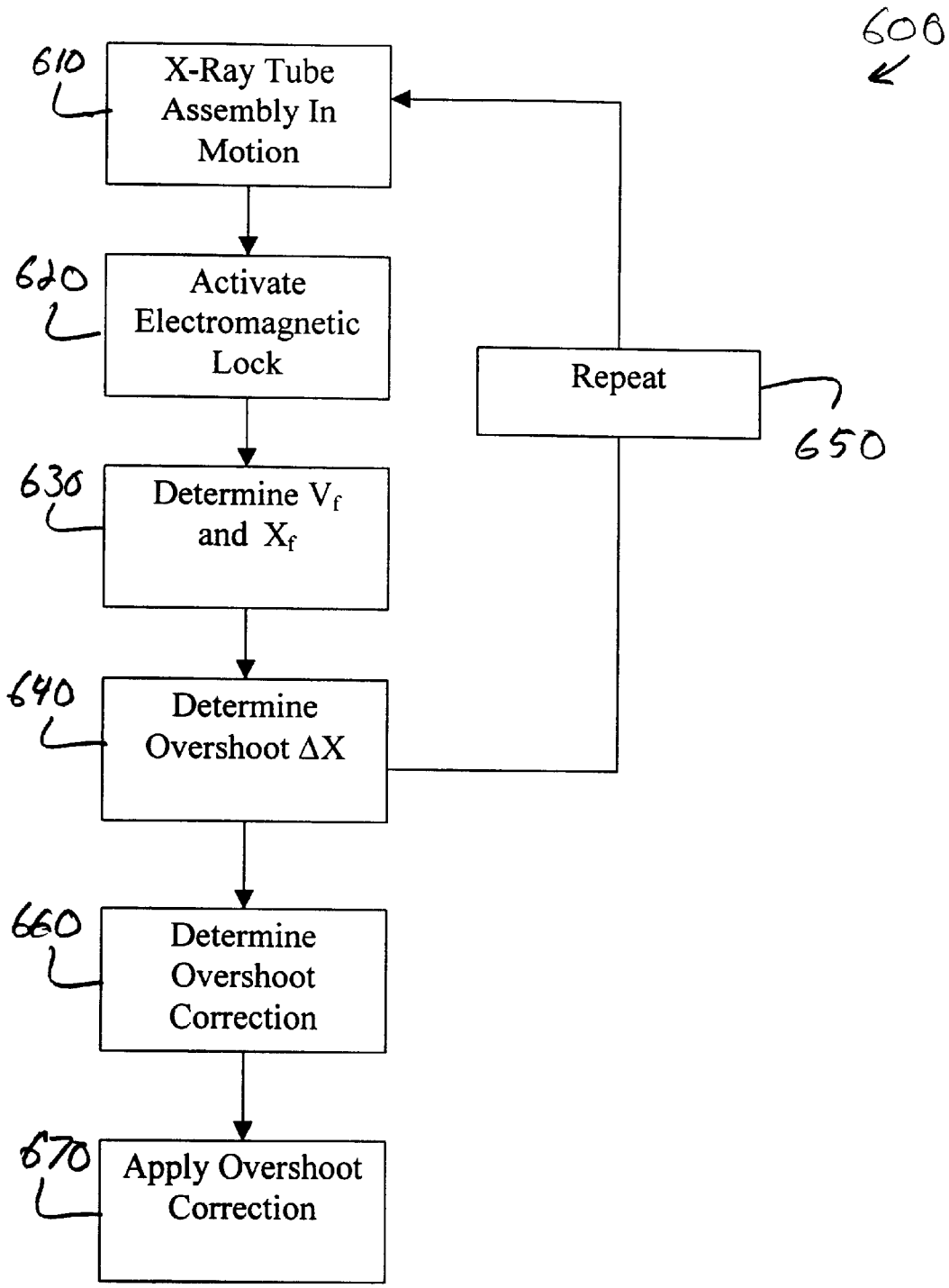
FIG. 6 illustrates a flowchart of the calibration system according to a preferred embodiment of the present invention.

FIG. 6 illustrates a flowchart 600 of the calibration system according to a preferred embodiment of the present invention. First, at step 610, the X-Ray tube assembly is in motion. At step 620, the electromagnetic lock is activated and the initial velocity $V_o$ and position $X_o$ are determined. Next, at step 630, the X-Ray tube assembly comes to a halt and the final velocity $V_f$ and position $X_f$ are determined. Then, at step 640, the initial $X_o$ and final positions $X_f$ are used to determine the overshoot $\Delta X$. Then, at step 650, steps 610 to 640 are repeated a predetermined number of times at differing initial velocities to generate an empirical relationship between the initial speed $V_o$ and the offset, $\Delta X$. Next, at step 660, the results of the repeated measurements at different initial velocities are used to determine an overshoot correction. Finally, at step 670, the overshoot correction is applied to the motion of the X-Ray tube assembly during clinical use. As mentioned above, to implement the third embodiment of the present invention, steps 610 to 640 may be repeated for each clinical positioning of the assembly.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for reducing positioning errors of an X-Ray tube relative to a target to be exposed in an X-Ray imaging device, said system including:
   an X-Ray tube, said X-Ray tube moveable relative to a target to be exposed in an X-Ray imaging device;
   a sensor unit generating positional signals indicative of the position of said X-Ray tube within the X-Ray imaging device; and
   a microprocessor receiving said positional signals and determining an overshoot correction for said X-Ray tube based on said positional signals and a predetermined X-Ray tube position relative to said target to be exposed within said X-Ray imaging device, said overshoot correction applied within said X-Ray device to adjust the motion of said X-Ray tube.

2. The system of claim 1 wherein the sensor unit uses a potentiometer to generate said positional signals.

3. The system of claim 1 wherein the sensor unit uses a digital encoder to generate said positional signals.

4. The system of claim 1 wherein said sensor unit generates velocity signals in addition to positional systems and said velocity signals are received by said microprocessor.

5. The system of claim 4 wherein said microprocessor determines said overshoot correction based on said positional and velocity signals.

6. The system of claim 5 further including a locking system.

7. The system of claim 6 wherein said locking system is an electromagnetic locking system.

8. The system of claim 6 wherein said microprocessor impacts the motion of said X-Ray tube by activating said locking system.

9. The system of claim 1 wherein said overshoot correction is determined by at least analyzing the initial and final positions of the X-Ray tube.

10. A sensor unit in an X-Ray imaging system including an X-Ray tube moveable relative to a patient, the sensor unit monitoring the position of the X-Ray tube, said sensor unit including:
    a position indicator generating position signals indicative of the position of an X-Ray tube within the X-Ray imaging system relative to said patient; and
    a microprocessor interface adapted to communicate with an external microprocessor to convey said positional signals to the external microprocessor.

11. The sensor unit of claim 10 wherein said positional indicator includes a digital encoder.

12. The sensor unit of claim 10 wherein said positional indicator includes a potentiometer.

13. The sensor unit of claim 10 wherein said positional indicator includes both a digital encoder and a potentiometer.

14. The sensor unit of claim 13 wherein said positional signals are generated by determining a start-up position using said potentiometer and thereafter determining position using said digital encoder.

15. The sensor unit of claim 10 wherein said positional indicator includes at least one position sensor belt.

16. The sensor unit of claim 15 wherein said position sensor belt is self-tensioning.

17. The sensor unit of claim 10 wherein said positional indicator also generates velocity signals indicative of the velocity of the X-Ray tube and said microprocessor interface allows an external microprocessor to receive said velocity signals.

18. A method of reducing positioning errors of an X-Ray tube relative to a target to be exposed in an X-Ray imaging system, said method including the step of:
    determining an overshoot correction for an X-Ray tube relative to a target to be exposed; and
    applying said overshoot correction to control the motion of said X-Ray tube to reduce positioning errors in the positioning of said X-Ray tube relative to said target to be exposed.

19. The method of claim 18 wherein said overshoot correction is determined by using positional data relating to the position of said X-Ray tube.

20. The method of claim 18 wherein said overshoot correction is determined by using velocity date relating to the velocity of said X-Ray tube.

21. The method of claim 18 further including the step of measuring at least positional data relating to the position of said X-Ray tube.

22. The method of claim 21 wherein said measuring step includes measuring at least positional data using a potentiometer.

23. The method of claim 21 wherein said measuring step includes measuring at least positional data using a digital encoder.

24. The method of claim 18 wherein said applying step controls the motion of said X-Ray tube by activating a locking system.

25. The method of claim 24 wherein said locking system is an electromagnetic locking system.

26. A method for determining an overshoot correction for use in reducing positioning errors of an X-Ray tube in an X-Ray imaging system, said method including the steps of:
    moving the X-Ray tube at a predetermined initial velocity;
    activating a locking system at an initial position to initiate halting the movement of said X-Ray tube;
    determining a final position at which the X-Ray tube comes to rest; and
    determining an overshoot correction based on the difference between the initial position and a final position.

27. The method of claim 26 further including the step of repeating the moving, activating, and determining steps at a predetermined different initial velocity at least once to determine a distribution for said overshoot correction based on said initial velocity and said different initial velocity.

28. The method of claim 26 further including comparing said final position with a predetermined, desired position and notifying an operator if said final position differs more than a predetermined distance from said desired position.

29. The method of claim 26 further including the step of repeating the moving, activating, and determining steps during clinical use of the X-Ray tube.

30. A system for reducing positioning errors of an X-Ray tube in an X-Ray imaging device, said system including:
    an X-Ray tube;
    a sensor unit generating positional signals and velocity signals indicative of the position and velocity of said X-Ray tube within the X-Ray imaging device; and
    a microprocessor receiving said positional signals and said velocity signals and determining an overshoot correction for said X-Ray tube based on said positional signals and velocity signals, said overshoot correction applied within said X-Ray device to adjust the motion of said X-Ray tube.

31. A sensor unit in an X-Ray imaging system including an X-Ray tube, the sensor unit monitoring the position and velocity of the X-Ray tube, said sensor unit including:
    a position indicator generating position signals indicative of the position of an X-Ray tube within the X-Ray imaging system;
    a velocity indicator generating velocity signals indicative of the velocity of said X-Ray tube within the X-Ray imaging system; and
    a microprocessor interface adapted to communicate with an external microprocessor to convey said positional signals and said velocity signals to the external microprocessor.

32. A method of reducing positioning errors of an X-Ray tube in an X-Ray imaging system, said method including the step of:
    determining an overshoot correction for an X-Ray tube based at least in part on the velocity of said X-Ray tube; and
    applying said overshoot correction to control the motion of said X-Ray tube to reduce positioning errors in the positioning of said X-Ray tube.

33. A method for determining an overshoot correction for use in reducing positioning errors of an X-Ray tube in an X-Ray imaging system, said method including the steps of:
    moving the X-Ray tube at a predetermined initial velocity;
    activating a locking system at an initial position to initiate halting the movement of said X-Ray tube;
    determining a final position at which the X-Ray tube comes to rest; and
    determining an overshoot correction based on a relation between the initial position and a final position and said predetermined velocity.

34. A method for determining an overshoot correction for use in reducing positioning errors of an X-Ray tube relative to a target to be exposed in an X-Ray imaging system, said method including the steps of:
    moving the X-Ray tube at a predetermined initial velocity;
    activating a locking system at an initial position to initiate halting the movement of said X-Ray tube;
    determining a final position at which the X-Ray tube comes to rest; and
    determining an overshoot correction to reduce positioning errors of said X-Ray tube relative to a target to be exposed based on the difference between the initial position and a final position.

* * * * *